(12) United States Patent
Hatano et al.

(10) Patent No.: US 11,805,978 B2
(45) Date of Patent: Nov. 7, 2023

(54) ENDOSCOPE OPERATION SECTION AND ENDOSCOPE INCLUDING ENDOSCOPE OPERATION SECTION

(71) Applicant: OLYMPUS CORPORATION, Tokyo (JP)

(72) Inventors: Keisuke Hatano, Koganei (JP); Tatsuhiko Suzuki, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 706 days.

(21) Appl. No.: 16/455,904

(22) Filed: Jun. 28, 2019

(65) Prior Publication Data
US 2019/0313886 A1 Oct. 17, 2019

Related U.S. Application Data

(63) Continuation of application No. PCT/JP2017/034311, filed on Sep. 22, 2017.

(30) Foreign Application Priority Data

Feb. 22, 2017 (JP) .................................. 2017-031193

(51) Int. Cl.
*A61B 1/00* (2006.01)
*A61B 1/005* (2006.01)
*A61B 1/018* (2006.01)

(52) U.S. Cl.
CPC ...... *A61B 1/00042* (2022.02); *A61B 1/00039* (2013.01); *A61B 1/0055* (2013.01);
(Continued)

(58) Field of Classification Search
None
See application file for complete search history.

(56) References Cited

U.S. PATENT DOCUMENTS 4,270,525 A * 6/1981 Furihata ................. A61M 1/76
600/154
4,617,915 A * 10/1986 Arakawa ................ A61B 1/042
600/102
(Continued)

FOREIGN PATENT DOCUMENTS

JP 2002200029 A * 7/2002 ............ A61B 1/005
JP 2004141331 A * 5/2004
(Continued)

OTHER PUBLICATIONS

International Search Report dated Nov. 7, 2017 issued in PCT/JP2017/034311.

*Primary Examiner* — Ryan N Henderson
(74) *Attorney, Agent, or Firm* — Scully, Scott, Murphy & Presser, P.C.

(57) ABSTRACT

An endoscope operation section of the present invention includes an operation section having a second longitudinal axis extending in a substantially same direction as a first longitudinal axis of an insertion section, the operation section being configured to be grasped by an operator, a bending operation member, including an axis crossing the second longitudinal axis at an acute angle during nonoperation, and configured to bend the insertion section, a first pedestal section to which a suction operation member is attached, a second pedestal section in which a surface projecting further in the forward direction by a predetermined height than the first pedestal section is formed, the predetermined height being set to a higher position in the forward direction than a position of a suction tube connecting member of the suction operation member, and a pressing operation member provided on the surface of the second pedestal section and pressed and operated.

18 Claims, 4 Drawing Sheets

(52) U.S. Cl.
CPC ........ *A61B 1/0057* (2013.01); *A61B 1/00066* (2013.01); *A61B 1/00068* (2013.01); *A61B 1/0052* (2013.01); *A61B 1/00094* (2013.01); *A61B 1/018* (2013.01)

(56) References Cited

U.S. PATENT DOCUMENTS

| | | | | |
|---|---|---|---|---|
| 4,721,099 | A * | 1/1988 | Chikama | A61B 1/00042 600/152 |
| 4,979,497 | A * | 12/1990 | Matsuura | A61B 1/042 600/921 |
| 5,573,494 | A * | 11/1996 | Yabe | A61B 1/0051 600/106 |
| 5,846,183 | A * | 12/1998 | Chilcoat | A61B 1/00165 600/120 |
| 8,403,831 | B2 * | 3/2013 | Kishioka | A61B 1/0052 600/131 |
| 8,961,402 | B2 * | 2/2015 | Okamoto | A61B 1/00042 600/146 |
| 9,936,860 | B2 * | 4/2018 | Okamoto | G02B 23/2476 |
| 2003/0092965 | A1 * | 5/2003 | Konomura | A61B 1/00048 600/152 |
| 2003/0195389 | A1 * | 10/2003 | Motoki | A61B 1/00042 600/104 |
| 2004/0034279 | A1 * | 2/2004 | Arai | A61B 1/0051 600/152 |
| 2004/0054258 | A1 * | 3/2004 | Maeda | A61B 1/00042 600/152 |
| 2004/0073085 | A1 * | 4/2004 | Ikeda | A61B 1/0051 600/101 |
| 2004/0193014 | A1 * | 9/2004 | Miyagi | A61B 1/05 600/118 |
| 2004/0267093 | A1 * | 12/2004 | Miyagi | A61B 1/009 600/152 |
| 2007/0030344 | A1 * | 2/2007 | Miyamoto | A61B 1/00052 348/65 |
| 2007/0161861 | A1 * | 7/2007 | Kawai | A61B 1/0051 600/152 |
| 2007/0249904 | A1 * | 10/2007 | Amano | A61B 1/0051 600/109 |
| 2008/0009677 | A1 * | 1/2008 | Shoroji | A61B 1/0051 600/160 |
| 2008/0021268 | A1 * | 1/2008 | Shoroji | A61B 1/0051 600/101 |
| 2008/0119696 | A1 * | 5/2008 | Moriyama | A61B 1/0052 600/146 |
| 2009/0036742 | A1 * | 2/2009 | Watanabe | A61B 1/0052 600/178 |
| 2009/0122574 | A1 * | 5/2009 | Ogawa | A61B 1/07 362/574 |
| 2009/0149709 | A1 * | 6/2009 | Koitabashi | A61B 1/00149 600/131 |
| 2011/0208002 | A1 * | 8/2011 | Kishioka | A61B 1/00052 600/146 |
| 2012/0172667 | A1 * | 7/2012 | Takeuchi | A61B 1/0055 600/140 |
| 2012/0209068 | A1 * | 8/2012 | Hosaka | G02B 23/2476 600/109 |
| 2013/0047755 | A1 * | 2/2013 | Okamoto | A61B 1/0052 74/89.2 |
| 2013/0060088 | A1 * | 3/2013 | Okamoto | A61B 1/0052 600/146 |
| 2013/0267775 | A1 * | 10/2013 | Okamoto | A61B 1/0016 600/109 |
| 2013/0274550 | A1 * | 10/2013 | Takeuchi | A61B 1/015 600/104 |
| 2013/0338441 | A1 * | 12/2013 | Okamoto | A61B 1/0052 600/146 |
| 2014/0100424 | A1 * | 4/2014 | Hoshino | A61B 1/00002 600/118 |
| 2015/0099927 | A1 * | 4/2015 | Sadoughi | A61M 16/0418 128/200.26 |
| 2016/0341241 | A1 | 11/2016 | Hosaka | |
| 2017/0143190 | A1 * | 5/2017 | Okada | A61B 1/0669 |
| 2017/0215697 | A1 * | 8/2017 | Hatano | A61B 1/0057 |
| 2018/0049625 | A1 * | 2/2018 | Nakade | A61B 1/00 |
| 2018/0064895 | A1 * | 3/2018 | Sadoughi | A61M 16/0463 |
| 2019/0014973 | A1 * | 1/2019 | Hatano | A61B 1/0052 |
| 2019/0216295 | A1 * | 7/2019 | Hatano | A61B 1/0052 |
| 2019/0217034 | A1 * | 7/2019 | Maslow | A61B 1/0661 |

FOREIGN PATENT DOCUMENTS

| | | | |
|---|---|---|---|
| JP | 2006149877 A * | 6/2006 | ........ A61B 1/00068 |
| JP | 2014-117338 A | 6/2014 | |
| JP | 5930255 B2 | 6/2016 | |
| WO | WO 2015/118705 A1 | 8/2015 | |
| WO | WO 2017/002423 A1 | 1/2017 | |

* cited by examiner

ENDOSCOPE OPERATION SECTION AND ENDOSCOPE INCLUDING ENDOSCOPE OPERATION SECTION

CROSS REFERENCE TO RELATED APPLICATION

This application is a continuation application of PCT/JP2017/034311 filed on Sep. 22, 2017 and claims benefit of Japanese Application No. 2017-031193 filed in Japan on Feb. 22, 2017, the entire contents of which are incorporated herein by this reference.

BACKGROUND OF THE INVENTION

1. Field of the Invention

The present invention relates to an endoscope operation section including a bending section in an insertion section inserted into a subject, a bending operation member for operating the bending section and a functional operation member for operating endoscope functions such as suction being provided in the endoscope operation section, and an endoscope including the endoscope operation section.

2. Description of the Related Art

Endoscopes have been widely used in a medical field and an industrial field. The endoscopes include a so-called flexible endoscope including an elongated insertion section having flexibility. In general, the flexible endoscope includes a bending section configured to be able bend, according to hand-side operation of a user, a distal end of the insertion section around a major axis (an insertion axis) of the insertion section.

The conventional endoscope of the type, in particular, an endoscope for bronchus and the like, includes a small-diameter insertion section. A bending section requiring only a small amount of force for bending and configured to bend at a small curvature radius is provided on a distal end side of the insertion section. On a proximal end side of the insertion section, a grasping section grasped by the user and an operation section configured by a plurality of operation members or the like provided on a surface of the grasping section are provided.

Note that the plurality of operation members or the like are a plurality of operation members for operating endoscope functions such as suction and are, more specifically, for example, besides a bending operation member, a suction operation member, and the like functioning as operation input sections, various operation switches of a pressing type or operation buttons of the pressing type.

In general, the endoscope of such a form is used by the user grasping, with one of a left hand and a right hand, the grasping section provided in the operation section. In this case, the grasping section is configured in a form suitable for the user to grasp using three fingers of a middle finger, a ring finger, and a little finger of one of the left hand and the right hand.

The bending operation member (e.g., a lever-like operation member) functioning as the operation input section is disposed in a position suitable for operation by a thumb of a hand on the same side for grasping the grasping section. The suction operation member and the various pressing operation switches and pressing operation buttons (hereinafter abbreviated as "suction operation member and other plurality of pressing operation members and the like") functioning as the other operation input sections are disposed in positions suitable for operation by an index finger of the hand on the same side for grasping the grasping section.

As the endoscope of such a form, endoscopes of various forms have been proposed and disclosed by, for example, Japanese Patent No. 5930255 and the like.

The endoscopes disclosed by Japanese Patent No. 5930255 and the like are configured in a form suitable for a user to grasp a grasping section of an operation section using, for example, three fingers of a middle finger, a ring finger, and a little finger of a left hand. In a position to which the user naturally extends a thumb of the same hand in a state in which the user grasps the grasping section with the three fingers, a lever-like bending operation member is projected outward from one side surface of the grasping section.

Further, in a position to which the user naturally extends an index finger of the same hand in the same state, that is, in a state in which the user grasps the grasping section with the three fingers and presses a tip ball part of a thumb of the same hand against the bending operation member, the suction operation member and the other plurality of pressing operation members and the like are disposed on another side surface of the grasping section, for example, as pressing operation members of a push button type.

In this case, the operation members (the suction operation member and the other plurality of pressing operation members and the like) mainly operated by the index finger are disposed within a range in which at least a vicinity of a tip of the index finger can be moved. The disposition of the operation members is contrived according to frequencies of use of functions allocated to the respective operation members.

Incidentally, in general, the conventional endoscope is operated in an endoscope system configured to sequentially photoelectrically convert optical images in a subject set as an observation target using an image pickup device or the like and record image data acquired by the photoelectric conversion as a still image or a moving image.

In recent years, in an electronic apparatus such as an endoscope system including an endoscope, for example, a related technique for generating and recording electronic image data has been remarkably improved. More specifically, for example, besides an image pickup device of a multipixel type that can acquire higher-resolution image data, an arithmetic circuit that can more quickly process image data outputted from the image pickup device, and the like, a larger-capacity storage medium and the like have been more inexpensively supplied. Therefore, in recent years, it has been becoming possible to easily record a large volume of high-definition image data more quickly and more inexpensively.

In the conventional endoscope system, recording of a subject is mainly often performed by still image data. However, in the endoscope system in recent years, recording of a subject is often performed by moving image data based on the improvement of the technical environment explained above.

SUMMARY OF THE INVENTION

An endoscope operation section in an aspect of the present invention includes: an operation section connected to a proximal end side of an elongated insertion section configured to be inserted into a subject, the insertion section including a suction channel inside and having a first longitudinal axis, the operation section having a second longitudinal axis extending in a substantially same direction as the first longitudinal axis, the operation section being configured to be grasped by an operator; a bending operation member provided in a proximal end portion of the operation section, including an axis crossing the second longitudinal axis at an acute angle during nonoperation, and configured to swing around a predetermined fulcrum to bend the insertion section; a first pedestal section formed in a first position on a distal end side relative to the bending operation member in the operation section, a suction operation member being attached to the first pedestal section to project in a forward direction with respect to the second longitudinal axis; a second pedestal section formed in a second position on the proximal end side of the first pedestal section in the operation section, a surface projecting in a substantially same direction as the projecting direction of the suction operation member and further in the forward direction by a predetermined height than the first pedestal section being formed in the second pedestal section, the predetermined height being set to a higher position in the forward direction than a position of a suction tube connecting member provided in the suction operation member; and a pressing operation member provided on the surface and pressed and operated.

An endoscope in an aspect of the present invention includes the endoscope operation section.

DETAILED DESCRIPTION OF THE PREFERRED EMBODIMENT

The present invention is explained below with reference to an embodiment shown in the figures. The respective drawings used for the following explanation schematically show components. In order to show the respective components in recognizable sizes on the drawings, dimensional relations, scales, and the like of the respective members are sometimes differentiated for each of the respective components and shown. Therefore, the present invention is not limited to only forms shown in the figures concerning the numbers of the respective components, shapes of the respective components, ratios of sizes of the respective components, relative positional relations among the respective components, and the like described in the respective drawings.

Embodiment

Figure 1:
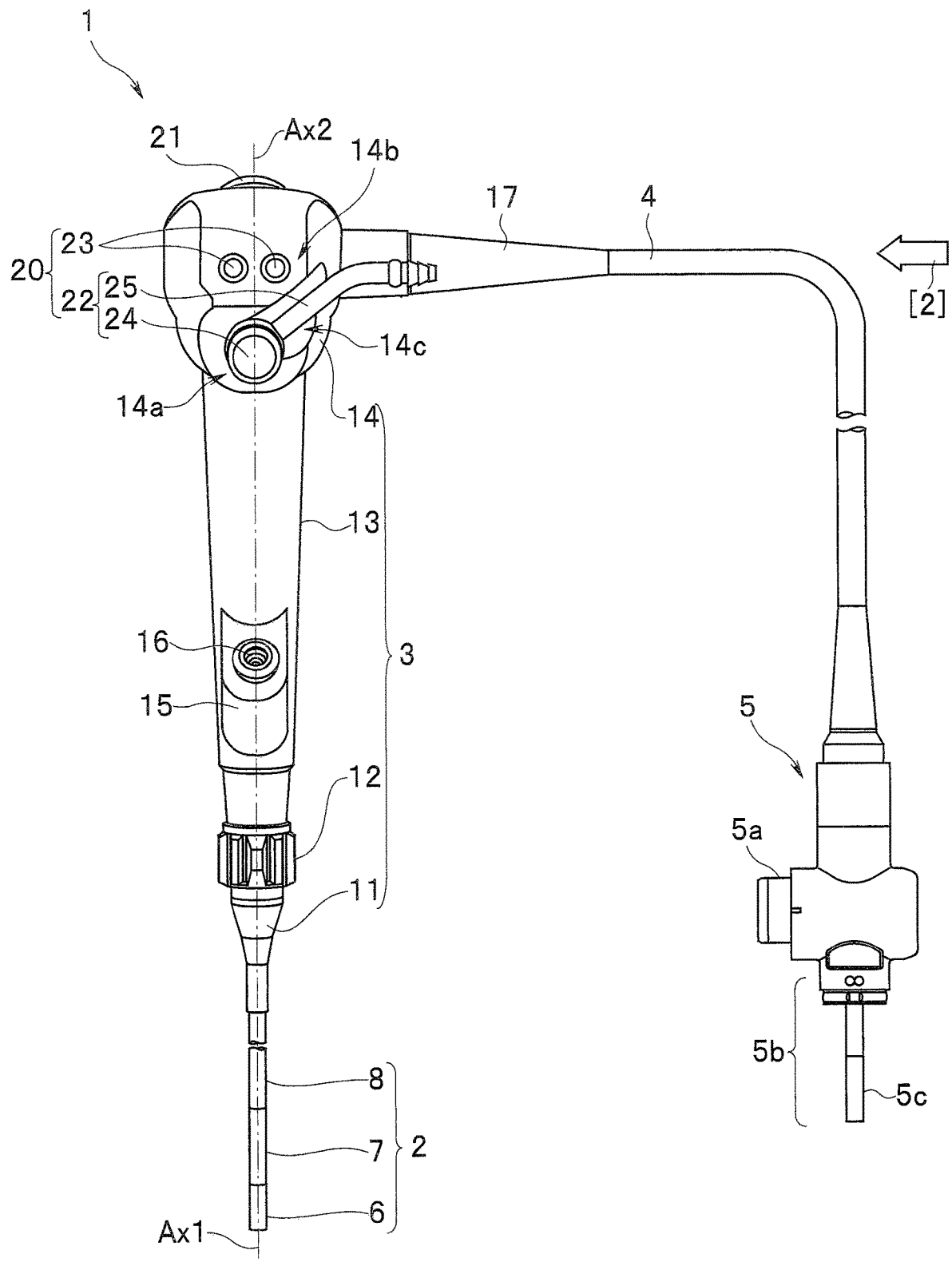
FIG. 1 is a front view showing a schematic configuration of an endoscope including an endoscope operation section in an embodiment of the present invention.
Figure 2:
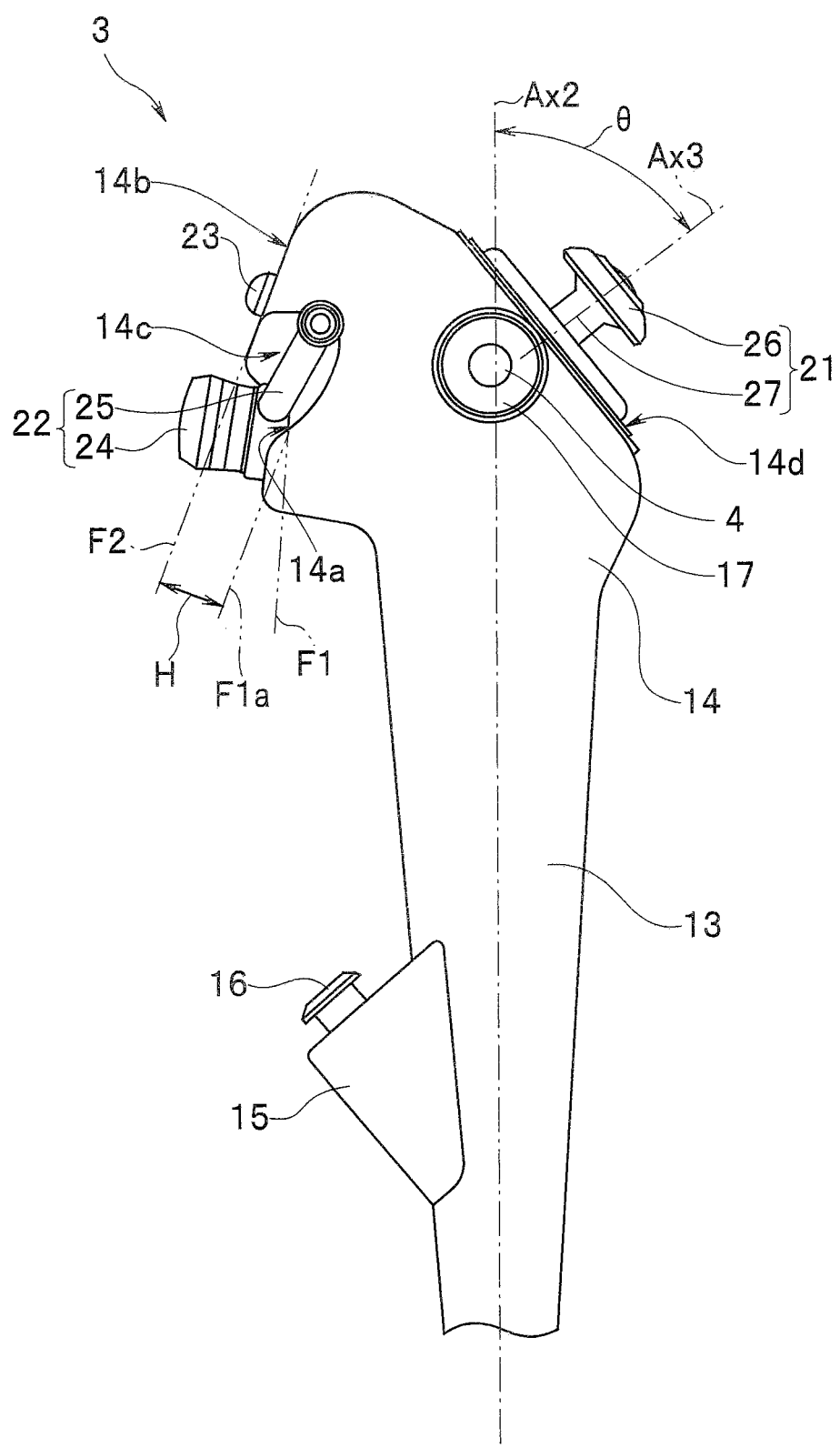
FIG. 2 is a main part enlarged side view (an arrow view viewed in an arrow sign [2] direction in FIG. 1) enlarging the endoscope operation section and showing one side surface (a left side surface) of the endoscope operation section in the endoscope in FIG. 1.
Figure 3:
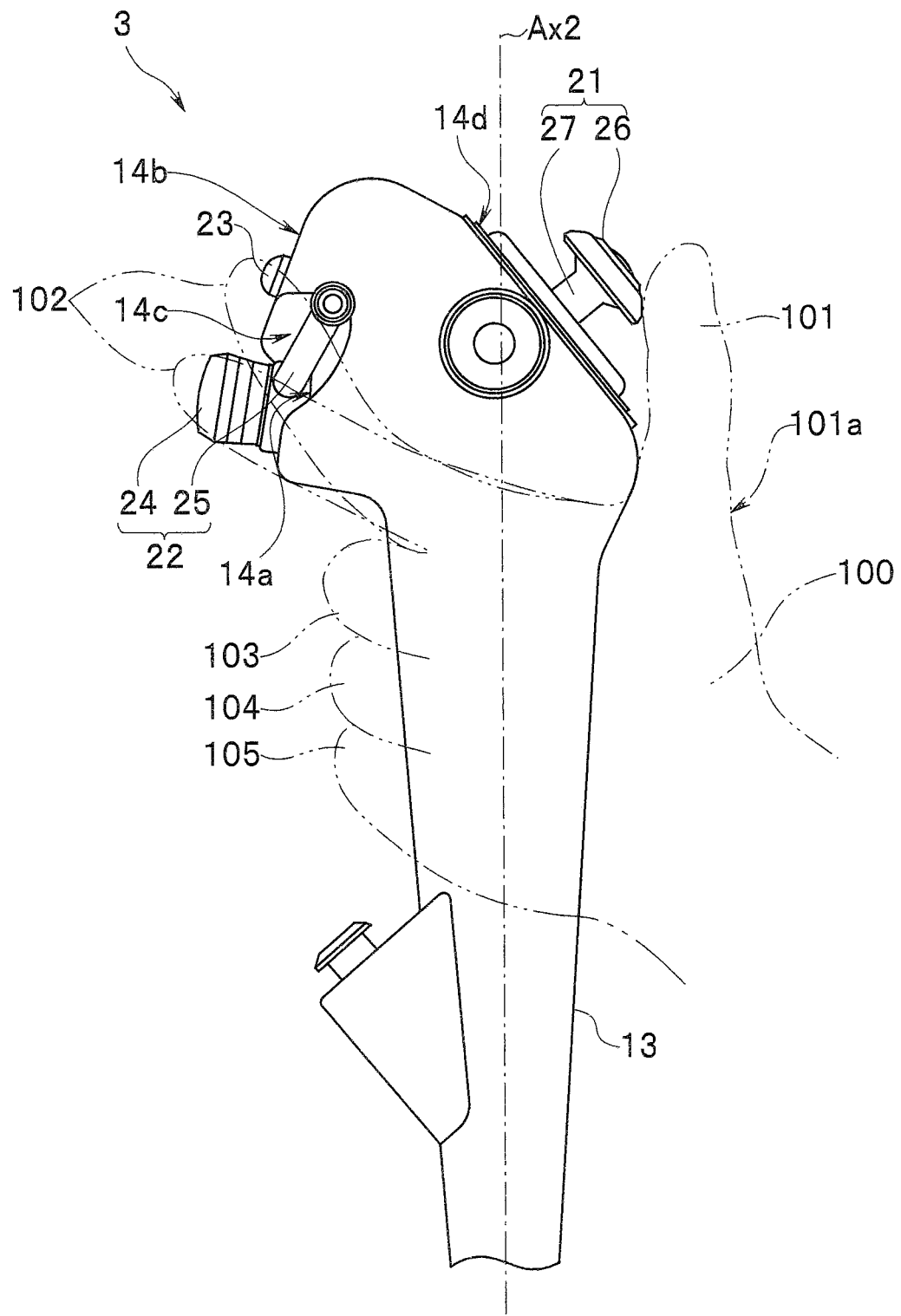
FIG. 3 is a side view showing a state in which a user grasps an operation section in a state of FIG. 2.

First, an endoscope in an embodiment of the present invention is explained with reference to the drawings. FIG. 1 is a front view showing a schematic configuration of an endoscope including an endoscope operation section in the embodiment of the present invention. FIG. 2 is a main part enlarged sectional view enlarging the endoscope operation section and showing one side surface (a left side surface) of the endoscope operation section in the endoscope in FIG. 1. FIG. 3 is a side view showing a state in which a user grasps an operation section in a state of FIG. 2. Note that FIG. 2 and FIG. 3 are arrow views viewed in an arrow sign [2] direction in FIG. 1.

An endoscope 1 in the embodiment is, for example, a small-diameter electronic endoscope for bronchus or for urinary organ. As shown in FIG. 1 and FIG. 2, the endoscope 1 is configured mainly by an insertion section 2 (see FIG. 1; not shown in FIG. 2), an endoscope operation section (hereinafter abbreviated as operation section) 3 interconnected to a proximal end of the insertion section 2, a universal cord 4, which is an endoscope cable, extended from the operation section 3, an endoscope connector 5 disposed at a distal end of the universal cord 4, and the like.

The insertion section 2 of the endoscope 1 is a component unit formed long in an elongated tubular shape and inserted into a subject. In the insertion section 2, as shown in FIG. 1, a distal end portion 6, a bending section 7, a flexible tube section 8 are interconnected in order from a distal end side. The insertion section 2 is configured as a tubular member having flexibility as a whole.

In the distal end portion 6 of the insertion section 2, although not shown in the figures, an image pickup unit incorporating an image pickup device (an image sensor) or the like such as an objective optical system, a CCD or a CMOS, an illumination optical system that irradiates illumination light transmitted by a light guide bundle (not shown in the figures) that allows insertion of the insertion section 2, the operation section 3, and the universal cord 4, a channel pipe (not shown in the figures) that connects and holds a treatment instrument channel (not shown in the figures) and the like are inserted through and disposed therein.

Note that an endoscope to which the present invention can be applied is not limited to the faun explained above, that is, the electronic endoscope including the image pickup unit and may be an endoscope of another form, for example, a configuration including an image fiber.

The bending section 7 of the insertion section 2 is configured to be able to be actively bent in all directions including upward, downward, left, and right directions around an insertion axis of the insertion section 2 according to an operation input of the user to the operation section 3. Note that a configuration of the bending section itself is not directly related to the present invention. Therefore, a detailed configuration of the bending section is omitted.

The flexible tube section 8 of the insertion section 2 is configured by a tubular member having flexibility to be able to passively bend.

Inside the insertion section 2, an image pickup cable, a light guide bundle, a treatment instrument insertion channel, a tube for air/water feeding, a suction channel, and the like are internally provided and inserted through (all of which are not shown in the figures).

Note that an insertion axis, which is a major axis in a longitudinal direction of the insertion section 2, is referred to as first longitudinal axis and is indicated by a sign Ax1 (see FIG. 1). In the following explanation, the first longitudinal axis is abbreviated as first axis Ax1.

In this way, the insertion section 2 is inserted into the subject and has the first axis Ax1. The suction channel is internally provided in the insertion section 2. The insertion section 2 is configured long in the elongated tubular shape.

The operation section 3 of the endoscope 1 is a component unit interconnected to a proximal end side of the insertion section 2 and grasped by the user, that is, an operator. A major axis in a longitudinal direction of the operation section 3 extending in the substantially same direction as the first axis Ax1 is referred to as second longitudinal axis and is indicated by a sign Ax2 (see FIG. 1). In the following explanation, the second longitudinal axis is abbreviated as second axis Ax2.

In other words, the operation section 3 is interconnected to the proximal end side of the insertion section 2, has the second axis Ax2 extending in the substantially same direction as the first axis Ax1, and is configured in a form suitably for the user, that is, the operator to grasp.

Explaining in detail, the operation section 3 is mainly configured by a bend preventing portion 11 connected to the flexible tube section 8 in a state in which the bend preventing portion 11 covers a proximal end of the flexible tube section 8, an insertion section rotation dial 12 provided on a proximal end side of the bend preventing portion 11 and configured to freely adjust a rotation position around the first axis Ax1, which is the insertion axis of the insertion section 2, a grasping section 13 interconnected to a proximal end side of the insertion section rotation dial 12 and graspable by a hand of the user or the like, an operation section main body 14 interconnected to a proximal end side of the grasping section 13.

Note that, in the embodiment, in indicating a direction around the second axis Ax2, which is the longitudinal axis in the operation section 3, a state in which the user grasps the grasping section 13 (see FIG. 3) is defined as a reference. In other words, more specifically, based on a visual point of the user (not shown in the figures) grasping the grasping section 13 of the operation section 3, a side surface of the endoscope 1 present in a right hand direction of the user is defined as a right side surface and a side surface (a surface shown in FIG. 2) of the endoscope 1 present in a left hand direction of the user is defined as a left side surface. A surface of the endoscope 1 opposed to the user is defined as a rear surface. A surface (a surface shown in FIG. 1) of the endoscope 1 opposed to the rear surface of the endoscope 1 is defined as a front surface.

The grasping section 13 is a part that the user grasps using three fingers of a middle finger, a ring finger, and a little finger of one of a left hand and a right hand. An example shown in FIG. 3 indicates a state in which the user is grasping the grasping section 13 using three fingers of a middle finger 103, a ring finger 104, and a little finger 105 of a left hand 100.

When viewed from a front, as shown in FIG. 1, the grasping section 13 is formed in a symmetrical shape with respect to the second axis Ax2. The user is capable of grasping the grasping section 13 in the same manner with any one of the left hand and the right hand.

A treatment instrument inserting section 15 is provided on a front side close to a distal end of the grasping section 13. The treatment instrument inserting section 15 includes a treatment instrument insertion opening 16 into which not-shown various treatment instruments are inserted.

A treatment instrument insertion channel (not shown in the figures) is caused to communicate with the treatment instrument insertion opening 16 via a branching member (not shown in the figures) inside the operation section 3. A lid member for closing the treatment instrument insertion opening 16, that is, for example, a disposable type forceps plug (not shown in the figures) is detachably disposed in the treatment instrument inserting section 15. Note that components around the treatment instrument inserting section 15 are portions not directly related to the present invention and are the same components as components included in the conventional endoscope. Therefore, illustration and explanation of detailed configurations of the components are omitted.

The operation section main body 14 is formed in a proximal end portion of the grasping section 13 and is configured mainly by a hollow member formed in a substantially partially spherical shape expanded to left and right sides and a front.

The operation section main body 14 is formed to include a plurality of inclined surfaces (14a, 14b, and 14d) formed at an inclination angle with respect to the second axis Ax2 when viewed from one side (e.g., see a left side in FIG. 2).

Among the plurality of inclined surfaces, the inclined surface indicated by a sign 14a in FIG. 1 and FIG. 2 is referred to as first inclined surface, the inclined surface indicated by a sign 14b in FIG. 1 and FIG. 2 is referred to as second inclined surface, and the inclined surface indicated by a sign 14d in FIG. 1 and FIG. 2 is referred to as third inclined surface.

Note that the first inclined surface 14a and the second inclined surface 14b are formed on a front side of the operation section main body 14. The third inclined surface 14d is formed on a rear side of the operation section main body 14.

In FIG. 2, a surface parallel to the first inclined surface 14a is indicated by an alternate long and two short dashes line F1. Similarly, in FIG. 2, a surface parallel to the second inclined surface 14b is indicated by an alternate long and two short dashes line F2.

As shown in FIG. 2, when the operation section main body 14 is viewed from one side (e.g., see the left side in FIG. 2), a step indicated by a sign H in FIG. 2 is formed in a position (see a sign F2 in FIG. 2) between a position (see a sign F1a in FIG. 2) where the first inclined surface 14a is provided and a position where the second inclined surface 14b is provided.

Further, as shown in FIG. 1, when the operation section main body 14 is viewed from a front, a cutout groove section 14c formed to cut out a part of the first inclined surface 14a to the second inclined surface 14b is formed.

Operation buttons 20 and the like including a plurality of operation members for executing a suction function, various optical system functions, and the like of the endoscope 1 are respectively disposed on the first inclined surface 14a and the second inclined surface 14b on the front side of the operation section main body 14.

The operation buttons 20 includes, for example, a suction valve 22 and a plurality of pressing operation members 23 of a push button type.

The suction valve 22 is an operation member detachably attached to the operation section main body 14. The suction valve 22 includes a suction button 24, which is a suction operation member functioning as an operation input member, and a suction tube connecting member 25.

Note that as the suction valve 22, for example, a suction valve of a disposable type is generally used. However, the suction valve 22 is not limited to the suction valve of the type and may be a suction valve of a reuse type.

The suction button 24 is disposed substantially in a center in a left-right width direction when viewed from the front side of the operation section main body 14. The suction button 24 is mounted on the first inclined surface 14a in an outer surface of the operation section main body 14. In this case, the suction button 24 is disposed to project in a substantially forward direction with respect to the second axis Ax2.

The suction tube connecting member 25 is a connecting member for connecting the suction button 24 and a not-shown suction tube extended from an endoscope aspirator, which is a not-shown external device. The suction tube connecting member 25 is formed by a rigid member having a hollow elongated tubular shape.

For example, as shown in FIG. 1, the suction tube connecting member 25 is formed in a form extending toward a side in an obliquely upward direction from a base section of the suction button 24 and thereafter extending in a side direction. A taper connecting section for securing connection to a not-shown suction tube is formed at a distal end portion of the suction tube connecting member 25.

The suction tube connecting member 25 is disposed in the cutout groove section 14c of the operation section main body 14. Consequently, the suction tube connecting member 25 is disposed to extend substantially sideward without interfering with the operation section main body 14.

On the other hand, the plurality of pressing operation members 23 of the push button type is pressing operation members of a pressing type to which any functions can be selectively allocated out of various functions concerning the endoscope 1.

In the embodiment, an example is explained in which two pressing operation members 23 are provided. An example is explained in which a freeze function and a release function among, for example, functions used in recording a still image are allocated to the plurality of pressing operation members 23 and the two pressing operation members 23 are used as remote switches for picking up image. In other words, the two pressing operation members 23 are pressing operation members concerning still image data recording.

Note that the plurality of pressing operation members 23 is not limited to the illustration. Three or more pressing operation members 23 may be provided. The endoscope functions allocated to each of the plurality of pressing operation members 23 are not limited to the above illustration.

In the embodiment, the number of the plurality of pressing operation members 23 is two. The two pressing operation members 23 are disposed side by side at a predetermined interval in the left-right width direction of the operation section main body 14, that is, a horizontal direction.

On the other hand, a bending operation lever 21, which is a bending operation member for performing bending operation for the bending section 7, is disposed on the third inclined surface 14d on the rear side of the operation section main body 14.

The bending operation lever 21 is, for example, a bar-like member of a so-called joystick type formed to be tiltable in all directions including the upward, downward, left, and right directions or an operation member of a tilting type configured by a lever member.

The bending operation lever 21 is configured by a support shaft 27 (see FIG. 2) and a finger contact section 26 provided at a distal end portion of the support shaft 27, the user bringing mainly a ball of the thumb into contact with the finger contact section 26 when the user performs tilting operation of the bending operation lever 21. The finger contact section 26 is disposed substantially in a center in the left-right width direction when viewed from the rear side of the operation section main body 14.

The support shaft 27 is disposed to be parallel to an axis Ax3 (see FIG. 2) crossing the second axis Ax2 at an acute angle (see a sign θ in FIG. 2) during nonoperation, that is, when the support shaft 27 is in a neutral position (see the state shown in FIG. 2). The support shaft 27 is configured to swing around a predetermined fulcrum (not shown in the figures) inside the operation section main body 14 and bend the bending section 7 of the insertion section 2.

In other words, the bending operation lever 21, which is the bending operation member, is an operation member provided on the third inclined surface 14d of the operation section main body 14 provided at a proximal end portion of the operation section 3 and, during nonoperation, having the axis Ax3 crossing the second axis Ax2 and configured to swing around the predetermined fulcrum (not shown in the figures) to bend the insertion section 2.

Note that a configuration of a bending mechanism itself in this case is not directly related to the present invention. Therefore, it is assumed that the configuration of the bending mechanism is the same as the configuration of the conventional endoscope. Illustration and explanation of a detailed configuration of the bending mechanism are omitted.

The user performs tilting operation of the bending operation lever 21 by bringing a thumb (a sign 101 in FIG. 3) of a hand (a sign 100 in FIG. 3) grasping the grasping section 13 into contact with the finger contact section 26 and pressing the finger contact section 26. Taking this into account, as shown in FIG. 3, the bending operation lever 21 is provided in a position closer to a proximal end in the operation section 3 than a position where a base 101a of the thumb 101 of the hand 100 is disposed when the user grasps the operation section main body 14.

On the other hand, the universal cord 4 is extended from a left side surface, which is one side surface, of the operation section main body 14 via a cable bend preventing portion 17. Note that, in this case, the universal cord 4 is extended from a position not interfering with the thumb 101 and an index finger 102, for example, the same position as the suction button 24 or a position on a proximal end side in a direction of the second axis Ax2 (see FIG. 2).

The universal cord 4 is a composite cable leading from the distal end portion 6 of the insertion section 2 to the operation section 3 through the inside of the insertion section 2. Various signal lines including an image pickup cable extending from the operation section 3, a light guide bundle, and a tube for air/water feeding into which fluid for air/water feeding is fed, and the like (all of which are not shown in the figures) are inserted through inside the composite cable.

The endoscope connector 5 is provided at an end part of the universal cord 4. The endoscope connector 5 includes an electric connector section 5a and a light source connector section 5b connected to a light source apparatus (not shown in the figures), which is an external device.

Note that the electric connector section 5a is a connecting section to which a connector (not shown in the figures) of an electric cable extended from a video processor, which is a not-shown external device, is detachably connected. The light source connector section 5b includes a light guide connector section 5c, in which the light guide bundle is housed, and a connector section for air/water feeding (not shown in the figures).

In the endoscope operation section 3 of the endoscope 1 in the embodiment configured as explained above, the first inclined surface 14a is a plane for attaching the suction button 24 explained below in the operation section main body 14 and is a first pedestal section in the operation section main body 14. The first inclined surface 14a, which is the first pedestal section, is formed in a first position (see signs F1 and F1a in FIG. 2) located on a distal end side in a direction along the second axis Ax2 relative to a position where the bending operation lever 21, which is the bending operation member, explained below in the operation section main body 14 is disposed. The suction button 24 (the suction operation member) explained below is attached to the first inclined surface 14a to project forward with respect to the second axis Ax2.

The second inclined surface 14b is a plane for disposing the plurality of pressing operation members 23 explained below in the operation section main body 14 and is a second pedestal section in the operation section main body 14. The second inclined surface 14b, which is the second pedestal section, is formed in a second position (see the sign F2 in FIG. 2) on a proximal end side of the first inclined surface 14a, which is the first pedestal section, explained below in the operation section main body 14.

Note that, in the embodiment, an example is explained in which a position of the pressing operation members 23 and a position of the finger contact section 26 of the bending operation lever 21 are substantially the same position in the direction of the second axis Ax2 (see FIG. 2). However, the position of the pressing operation members 23 may be on the insertion section 2 side or may be on a proximal end side (an upper side in FIG. 2) in the second axis Ax2 direction relative to the finger contact section 26.

The second inclined surface 14b is formed as a surface projecting forward by a predetermined height H (see FIG. 2) relative to the first inclined surface 14a, which is the first pedestal section, in substantially the same direction as a projecting direction of the suction button 24 (the suction operation member) explained below. In this case, the predetermined height H is set forward in a higher position than a position (see the sign F1a in FIG. 2) of the suction tube connecting member 25 provided in the suction button 24 (the suction operation member). The plurality of pressing operation members 23 functioning as the pressing operation members to be pressed and operated are provided on the second inclined surface 14b.

Simply speaking, the operation section 3 of the endoscope 1 in the embodiment is configured such that an operation member (the suction button 24 of the suction valve 22) having a high frequency of use is disposed in a position closer to a finger (e.g., the middle finger) grasping the grasping section 13 than, for example, a pressing operation member (the two pressing operation members 23 concerning still image data recording) having a low frequency of use among the plurality of pressing operation members provided in the operation section main body 14 and operated mainly by the index finger.

Further, the plurality of (two) pressing operation members 23 are configured to be disposed on a surface (the second inclined surface 14b; the second pedestal section) projecting forward relative to a surface (the first inclined surface 14a; the first pedestal section) on which the suction button 24 is disposed. The other components are substantially the same as the components of the conventional endoscope.

Action of the endoscope 1 in the embodiment is briefly explained below. When using the endoscope 1 in the embodiment configured as explained above, first, as shown in FIG. 3, the user grasps the grasping section 13 using, for example, the three fingers of the middle finger 103, the ring finger 104, and the little finger 105 of the left hand 100. At this time, the user brings the ball of the thumb 101 of the grasping left hand 100 into contact with the finger contact section 26 of the bending operation lever 21.

The index finger 102 of the same left hand 100 is present in a position where the index finger 102 can press and operate either the suction button 24 of the suction valve 22 or one of the two pressing operation members 23. Therefore, when desired, the user can press and operate either the suction button 24 of the suction valve 22 or one of the two pressing operation members 23 using the index finger 101 of the left hand 100.

In this case, when the user presses and operates either the suction button 24 of the suction valve 22 or one of the two pressing operation members 23 using the index finger 102, the suction tube connecting member 25 of the suction valve 22 is provided within a moving range of the index finger 102.

However, in the configuration in the embodiment, the second inclined surface 14b, on which the two pressing operation members 23 are provided, is formed in a position projecting forward relative to the first inclined surface 14a, on which the suction valve 22 is provided. Therefore, when the user operates one of the two pressing operation members 23, the finger (the index finger 102) that operates the pressing operation members 23 does not interfere with the suction tube connecting member 25 extending from a base section of the suction valve 22.

Note that, at this time, when it is unnecessary to operate any one of the suction button 24 and the two pressing operation members 23, the index finger 102 is used as a support for grasping the operation section main body 14 by being placed in, for example, a part where the suction button 24 is not provided on the first inclined surface 14a or in a vicinity of a base section of the suction button 24 or placed in, for example, a position where the pressing operation members 23 are not provided on the second inclined surface 14b.

As explained above, according to the embodiment, the operation section 3 of the endoscope 1 is configured such that the operation member (the suction button 24) having a high frequency of use is disposed in the position closer to the finger (e.g., the middle finger) grasping the grasping section 13 than, for example, the pressing operation members 23 having a low frequency of use among the plurality of operation members provided in the operation section main body 14 and operated by a specific finger (mainly the index finger).

By adopting such a configuration, when the operation member (the suction button 24) having a high frequency of use is operated by the index finger, it is possible to reduce a movement amount of the index finger. Accordingly, the configuration of the embodiment can contribute to improvement of operability.

According to the embodiment, the plurality of (two) pressing operation members 23 are configured to be disposed on the surface (the second inclined surface 14b; the second pedestal section) projecting forward relative to the surface (the first inclined surface 14a; the first pedestal section) on which the suction button 24 is disposed. In other words, the step having the predetermined height H is provided between the first inclined surface 14a and the second inclined surface 14b. In this case, in the operation section main body 14, the cutout groove section 14c, in which the suction tube connecting member 25 is disposed, is provided.

By adopting such a configuration, when the user grasps the grasping section 13 and operates the suction button 24 and the plurality of (two) pressing operation members 23 with the index finger of the grasping hand, it is possible to prevent the operating finger (the index finger) from interfering with the suction tube connecting member 25. Accordingly, the configuration of the embodiment can obtain satisfactory operability.

The endoscope 1 in the embodiment explained above is configured such that the plurality of pressing operation members 23 are disposed side by side at the predetermined interval in the left-right width direction of the operation section main body 14 (the horizontal direction). However, the disposition of the plurality of pressing operation members 23 is not limited to the illustration of the embodiment explained above and may be other different disposition forms.

A modification concerning a disposition form of the plurality of pressing operation members (23) in the endoscope is explained below.

Modification

Figure 4:
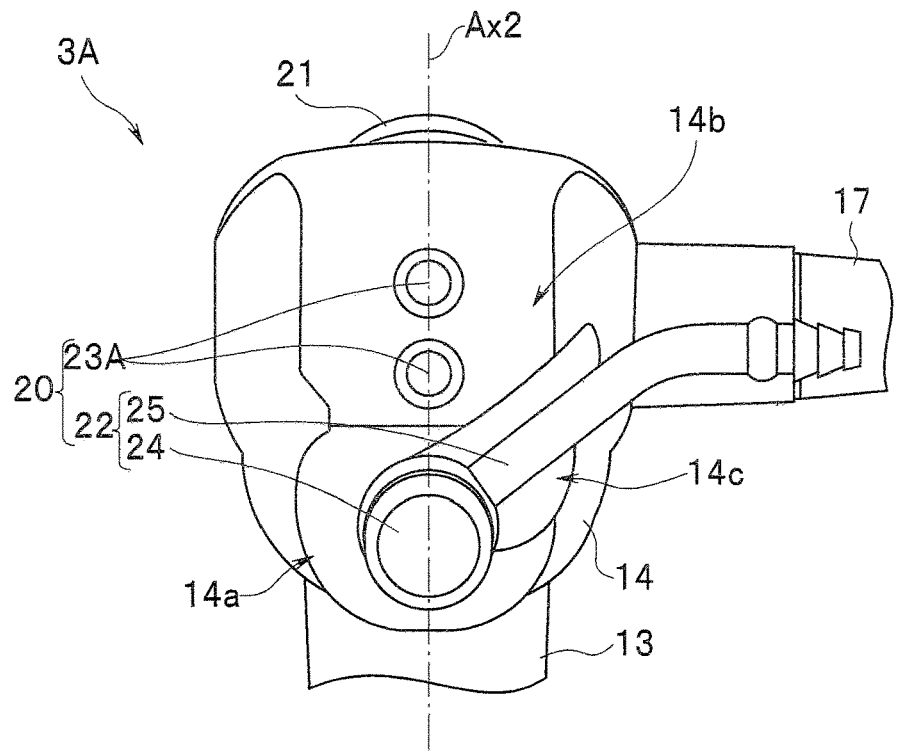
FIG. 4 is an enlarged front view showing a modification of the endoscope operation section in the embodiment of the present invention.
Figure 5:
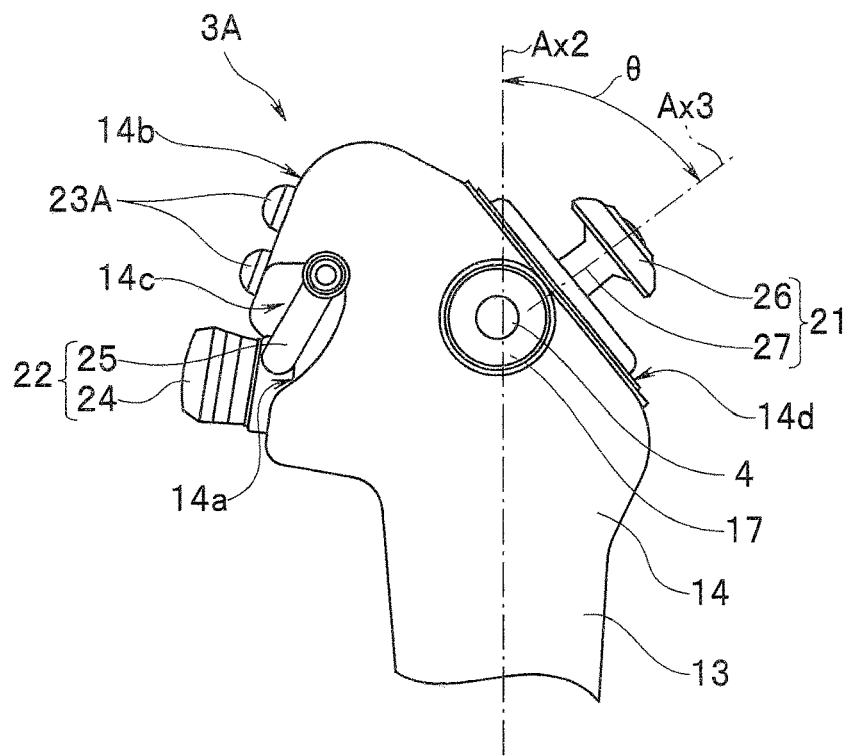
FIG. 5 is a main part enlarged side view showing one side surface (a left side surface) of the endoscope operation section in FIG. 4.

FIG. 4 and FIG. 5 are diagrams showing a modification of the endoscope operation section in the embodiment of the present invention. FIG. 4 is an enlarged front view of the modification. FIG. 5 is a main part enlarged side view showing one side surface (a left side surface) of the endoscope operation section shown in FIG. 4.

In an endoscope operation section 3A in the modification, a plurality of (two) pressing operation members 23A is configured to be disposed side by side at a predetermined interval in an up-down direction (a longitudinal direction) along the second axis Ax2 of the operation section main body 14. The other components are the same as the components in the embodiment explained above.

With the modification having such a configuration, it is possible to obtain completely the same effects as the effects in the embodiment explained above.

With the configuration of the modification, a distance from a position of the finger (the index finger) grasping the grasping section 13 to a position of each of the plurality of (two) pressing operation members 23A can be set to be a substantially equal distance. Therefore, when operating the plurality of (two) pressing operation members 23A, the user can comfortably move the finger (the index finger). Therefore, it is possible to obtain more satisfactory operability.

Note that, as another form of the modification explained above, disposition of the pressing operation members explained below is also conceivable. The plurality of (two) pressing operation members may be disposed side by side at a predetermined interval along an imaginary line having a predetermined inclination angle with respect to the second axis Ax2.

When such a configuration is adopted, considering a moving range of the index finger of the hand grasping the grasping section, the imaginary line is desirably set to extend in an oblique direction having a predetermined inclination angle with respect to the second axis Ax2 from an upper side of the operation section toward a side where the hand grasps the grasping section.

If such a configuration is adopted, the pressing operation member on a lower side is disposed on a side closer to the hand grasping the grasping section than the pressing operation member on an upper side. Therefore, by naturally moving the index finger, it is possible to dispose all of the plurality of pressing operation members to be able to comfortably perform pressing operation.

The present invention is not limited to the embodiment explained above. It goes without saying that it is possible to carry out various modifications and applications within a range not departing from the gist of the invention. Further, inventions at various stages are included in the embodiment. Various inventions can be extracted according to appropriate combinations in a disclosed plurality of constituent elements. For example, when the problems to be solved by the invention can be solved and the effects of the invention can be obtained even if several constituent elements are deleted from all the constituent elements described in the embodiment, a configuration from which the constituent elements are deleted can be extracted as an invention. Further, constituent elements in different embodiments may be combined as appropriate. The present invention is not restricted by specific embodiment of the invention other than being limited by the appended claims.

The present invention can be applied to not only an endoscope in a medical field but also an endoscope in an industrial field.

What is claimed is:

1. An endoscope operation section comprising:
   an operation body having a longitudinal axis, the operation body comprising:
   a bending operation lever provided at the operation body, the bending operation lever configured to be operated around an axis offset at an angle with respect to the longitudinal axis;
   a first surface projecting a first distance from the longitudinal axis in a projecting direction,
   a suction button projecting in the projecting direction and extending from the first surface;
   a second surface on a proximal end side of the first surface, the second surface projecting a second distance from the longitudinal axis in the projecting direction, the second distance being greater than the first distance; and
   a switch provided on the second surface; and
   the operation body comprises:
   a suction channel inside the operation body;
   a concavity cut out from one or more of the first surface and the second surface; and
   a suction tube connecting member disposed in the concavity, the suction tube connecting member being configured to be in fluid communication with the suction channel.

2. The endoscope operation section according to claim 1, wherein the switch compresses a plurality of switches each provided on the second surface.

3. The endoscope operation section according to claim 2, wherein the plurality of switches are disposed side by side at a predetermined interval in a direction perpendicular to a longitudinal axis direction.

4. The endoscope operation section according to claim 2, wherein the plurality of switches are disposed side by side at a predetermined interval in a longitudinal axis direction.

5. An endoscope comprising the endoscope operation section according to claim 1; and
   an elongated insertion portion comprising a suction channel.

6. The endoscope operation section according to claim 1, wherein the switch projects from the second surface in the projecting direction.

7. The endoscope operation section according to claim 1, further comprising a universal cord extending radially from the operation body, the universal cord being offset circumferentially from the concavity.

8. The endoscope operation section according to claim 1, wherein an end surface of the suction button projects a third distance in the projecting direction, the third distance being greater than the second distance.

9. The endoscope operation section according to claim 1, wherein the bending operation lever is provided at a third surface opposite to each of the first surface and the second surface relative to the longitudinal axis.

10. The endoscope operation section according to claim 1, further comprising an insertion section connected to a distal end of the operation body, the insertion section being configured to bend and to be inserted into a subject.

11. The endoscope operation section according to claim 1, wherein the projecting direction is offset at an angle with respect to the longitudinal axis.

12. The endoscope operation section according to claim 1, wherein the bending operation lever is provided in a proximal end portion of the operation body, and the axis of the bending operation lever crosses the longitudinal axis at an acute angle during nonoperation, and is configured to swing around a predetermined fulcrum.

13. The endoscope operation section according to claim 1, wherein
the first surface is provided on a first pedestal section formed on a distal end side of the operation section body relative to the bending operation lever; and
the second surface is provided on a second pedestal section formed on a proximal end side of the operation section body relative to the first surface.

14. An endoscope operation section comprising:
an operation body connected to a proximal end side of an elongated insertion section configured to be inserted into a subject, the insertion section comprising a suction channel inside and the insertion section having a first longitudinal axis, the operation body having a second longitudinal axis extending in a substantially same direction as the first longitudinal axis, the operation body being configured to be grasped by an operator;
a bending operation lever provided in a proximal end portion of the operation body, including an axis crossing the second longitudinal axis at an acute angle during nonoperation, and configured to swing around a predetermined fulcrum to bend the insertion section;
a first pedestal section formed in a first position on a distal end side relative to the bending operation lever in the operation body, a suction button extending from a first surface of the first pedestal section, the first surface projecting a first distance from the second longitudinal axis in a projecting direction of the suction button;
a suction tube connecting member configured to connect to one end of a suction tube, the suction tube connecting member extending from the suction button;
a second pedestal section formed in a second position on the proximal end side of the first pedestal section in the operation body, the second pedestal being fixed relative to the first pedestal section, the second pedestal having a second surface projecting a second distance from the second longitudinal axis in the projecting direction of the suction button, the second distance being greater than the first distance; and
a switch provided on the second surface, the switch being configured to be operated by pressing; and
the operation body comprises:
a suction channel inside the operation body;
a concavity cut out from one or more of the first surface and the second surface; and
the suction tube connecting member being disposed in the concavity, the suction tube connecting member being configured to be in fluid communication with the suction channel.

15. The endoscope operation section according to claim 14, wherein the operation body comprises a concavity cut out from each of the first surface and the second surface.

16. The endoscope operation section according to claim 15, further comprising a universal cord extending radially from the operation body, the universal cord being offset circumferentially from the concavity.

17. The endoscope operation section according to claim 14, wherein an end surface of the suction button projects a third distance in the projecting direction, the third distance being greater than the second distance.

18. An endoscope operation section comprising:
an operation body having a longitudinal axis, the operation body comprising:
a bending operation lever provided at the operation body, the bending operation lever configured to be operated around an axis offset at an angle with respect to the longitudinal axis;
a first surface projecting a first distance from the longitudinal axis in a projecting direction,
a suction button projecting in the projecting direction and extending from the first surface;
a second surface on a proximal end side of the first surface, the second surface being fixed relative to the first surface, the second surface projecting a second distance from the longitudinal axis in the projecting direction, the second distance being greater than the first distance; and
a switch provided on the second surface;
wherein the operation body further comprising a concavity cut out from one or more of the first surface and the second surface; and
the operation body comprises:
a suction channel inside the operation body; and
a suction tube connecting member disposed in the concavity, the suction tube connecting member being configured to be in fluid communication with the suction channel,
wherein the first and second surfaces being coincident with first and second planes, respectively, and each of the first and second planes intersect the longitudinal axis.

* * * * *